United States Patent
Sabbahi (10) Patent No.: US 10,828,190 B2
(45) Date of Patent: Nov. 10, 2020

(54) AIR FLOW SYSTEM AND METHOD FOR AIR CIRCULATION THERAPY

(71) Applicant: Wesam Sabbahi, Houston, TX (US)

(72) Inventor: Wesam Sabbahi, Houston, TX (US)

( * ) Notice: Subject to any disclaimer, the term of this patent is extended or adjusted under 35 U.S.C. 154(b) by 439 days.

(21) Appl. No.: 15/764,850

(22) PCT Filed: Sep. 30, 2016

(86) PCT No.: PCT/US2016/054952
§ 371 (c)(1),
(2) Date: Mar. 29, 2018

(87) PCT Pub. No.: WO2017/059333
PCT Pub. Date: Apr. 6, 2017

(65) Prior Publication Data
US 2018/0263811 A1 Sep. 20, 2018

Related U.S. Application Data (60) Provisional application No. 62/235,169, filed on Sep. 30, 2015.

(51) Int. Cl.
*A61F 7/00* (2006.01)

(52) U.S. Cl.
CPC .............. *A61F 7/0085* (2013.01); *A61F 7/00* (2013.01); *A61F 7/0053* (2013.01); *A61F 7/0097* (2013.01); *A61F 2007/006* (2013.01); *A61F 2007/0052* (2013.01); *A61F 2007/0055* (2013.01); *A61F 2007/0057* (2013.01); *A61F 2007/0064* (2013.01); *A61F 2007/0072* (2013.01); *A61F 2007/0086* (2013.01); *A61F 2007/0091* (2013.01); *A61F 2007/0093* (2013.01); *A61F 2007/0095* (2013.01); *A61F 2007/0096* (2013.01)

(58) Field of Classification Search
CPC combination set(s) only.
See application file for complete search history.

(56) References Cited

U.S. PATENT DOCUMENTS

| | | |
|---|---|---|
| 4,007,737 A | 2/1977 | Bernard |
| 2013/0238042 A1 | 9/2013 | Gildersleeve |
| 2014/0102452 A1 | 4/2014 | Forrester |

FOREIGN PATENT DOCUMENTS

SU  1174028 A  8/1985

*Primary Examiner* — Joseph A Stoklosa
*Assistant Examiner* — Adam J Avigan
(74) *Attorney, Agent, or Firm* — Craft Chu PLLC; Andrew W. Chu (57) ABSTRACT

The air flow system includes a hose member having an exterior flow tube and an interior flow tube, a distal connector, and a proximal connector. The air flow in the interior flow tube is separate from the exterior flow tube. Air flows from the exterior flow tube, through a flow chamber, around a treatment site of inflammation and back to the interior flow tube. The system for air circulation therapy also includes a body attachment device, an air pump supply, an air recovery unit, a temperature sensor, an air flow sensor, and a controller. The method includes inserting a body part with a treatment site within the flow chamber—and sealing the flow chamber to the air flow system. Temperature regulated air flow is supplied to the treatment site in the flow chamber and collected from the flow chamber.

20 Claims, 5 Drawing Sheets

AIR FLOW SYSTEM AND METHOD FOR AIR CIRCULATION THERAPY

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to a system and method for air circulation therapy. The present invention relates to an air flow system supplying air with temperature, speed and direction control. The present invention relates to a system for air circulation or air convection therapy. More particularly, the present invention relates to an air flow with temperature controlled to treat inflammation and for rehabilitation of injury. Even more particularly, the present invention relates to a method for treating inflammation at a treatment site in a flow chamber receiving controlled air from an air flow system.

2. Description of Related Art Including Information Disclosed Under 37 CFR 1.97 and 37 CFR 1.98

Pain, heat, redness, swelling, and loss of function are the responses to inflammation in the body. Inflammation is a protective response to harmful stimuli, such as damaged cells from a soft tissue injury, a germ or even a virus, or irritants. Inflammation is part of the immune system, as a defense system of the body, involving immune cells, other molecules, and blood flow. In particular, white blood cells and chemicals of the immune system can fight infection and foreign substances, such as bacteria and viruses. Inflammation begins tissue repair and removes dead or damaged cells from the tissue.

Acute inflammation moves blood into the injured tissue, usually as an initial reaction to an injury. Plasma and white bloods cells may be the first to arrive, but eventually a full immune response is brought to the injured tissue. Chronic inflammation is a protracted exposure of the injured tissue to the new cells triggered by the immune response. New damage to the tissue is caused by the inflammation, while the inflammation repairs the tissue at the same time.

Treatments for inflammation are known. Medication can address the pain aspect. Conventional treatments also include RICE (Rest, Ice, Compression and Elevation). Rest reduces the strain on the injured tissue. Ice or cold therapy causes vasoconstriction, which limits blow flow to the injured tissue. Compression and Elevation also address swelling and pain of inflammation.

In the area of cold therapy, ice packs are basic treatments. A cloth covered ice pack can be applied to the injured tissue. However, there are limitations. Ice packs can only be effective at limited exposures. An ice pack can cause cold burns and frostbite, if placed on or directly against injured tissue for too long, especially for elderly individuals with thinner skin.

It is also known to use heat therapy to treat inflammation, usually for rehabilitation purposes. The increased blood flow releases joint stiffness, decreases pain, and brings oxygen to the injured, yet healing, tissues.

While cold therapy has traditionally been used for acute inflammation and initial treatment of an injury, and heat therapy has traditionally been used for rehabilitation purpose, there is a need for a system to provide both as temperature controlled therapy.

In the past, various patents and patent publications have disclosed systems for temperature control therapy include both cold therapy and heat therapy.

U.S. Pat. No. 8,105,370, issued to Augustine, Scott on 31 Jan. 2012, discloses an inflatable thermal blanket. The inflatable blanket delivers airflow to the body and therapy site. There is a surgical drape as a window through the blanket so that surgeons can reach through the blanket and into the patient for surgery. The blanket control temperature of the body and therapy site or surgical site by controlling hot or cold air through the blanket.

U.S. Patent Publication No. 20110098792, published for Lowe, Mark H. et al on 28 Apr. 2011, teaches a therapeutic wrap for temperature-controlled therapy. A fluid bladder having an inlet, an outlet, and at least one fluidic channel is incorporated into the therapeutic wrap. Controlling the temperature of the fluid flowing through the fluidic channel controls the delivery of hot or cold to the therapy site, when the wrap is worn on the body part with the therapy site. The therapy wrap may include insulating layers to further control the delivery of hot or cold to the therapy site.

U.S. Patent Publication No. 20150216718, published for Diller, Kenneth R., et al on 6 Aug. 2015, describes another device for thermoelectric heating and cooling of mammalian tissue. A plurality of thermoelectric modules with temporal and spatial dimensions is placed on the tissue. Each module can be controlled to deliver hot or cold to the surface of the tissue and the coordination of modules can deliver set patterns of hot and cold in programmed sequences and different durations.

In the prior art, it is also known to deliver hot and cold by fluid or air flow. Air flow is known to be temperature controlled so as to provide a heat source and cool source to a therapy site on the body.

U.S. Patent Publication No. 20130238042, published for Gildersleeve, Richard et al, on 12 Sep. 2013, discloses a system and method for providing temperature-controlled therapy. A therapeutic wrap delivers temperature-controlled air or other gas to the therapy site on the body of the patient. Intended for orthopedic or other injuries, the therapy site is exposed to different temperatures for a variable amount of time. There are also feedback mechanisms for patient control of the temperature of the gas.

U.S. Patent Publication No. 20090270910, published for Hargens, Alan R., et al on 29 Oct. 2009, describes a method and apparatus for increasing blood flow in a body part. An enclosure is fitted to house an affected area of a body part. The enclosure is releasably sealed on the body part around the affected area, so as to form a substantially airtight enclosure. Air is pumped through a port to inflate the enclosure around the body part without contacting the area to be treated. The compression provided by the air pressure increases blood flow to the affected area without physically contacting the affected area. The pump is an air and vacuum pump for higher or lower pressure on the affected area.

It is an object of the present invention to provide a system for air circulation or air circumvection therapy.

It is an object of the present invention to provide a system for air convection therapy.

It is an object of the present invention to provide a system for air flow therapy with temperature control.

It is another object of the present invention to provide a system with controlled air flow for circulation therapy.

It is another object of the present invention to provide a system for temperature controlled therapy based on air convection.

It is still another object of the present invention to provide a system with controlled air flow and temperature control for treating inflammation.

It is yet another object of the present invention to provide an air flow system to control supplying air at a first temperature and recovering air at a second temperature from a flow chamber.

It is yet another object of the present invention to provide an air flow system to control a flow path of air supplied to a flow chamber and recovered from the flow chamber.

It is yet another object of the present invention to treat inflammation at a treatment site on a patient's body air flow at a regulated temperature.

It is yet another object of the present invention to adjust treatment by changing air flow speed and air temperature together.

These and other objectives and advantages of the present invention will become apparent from a reading of the attached specification.

BRIEF SUMMARY OF THE INVENTION

Embodiments of the present invention include the air flow system for supplying air at first temperature and a first speed and recovering air at a second temperature and a second speed. The flow path traveled by the air supplied includes circulating around inflammation on a body part of a patient and returning to the air flow system. The air flow system includes a hose member having an exterior flow tube forming an exterior flow channel, and an interior flow tube forming an inner flow channel. The interior flow channel recovers air, while the exterior flow channel supplies or delivers air.

The air flow system includes a distal connector having an outer sleeve with an outer sleeve flow channel and an inner sleeve with an inner sleeve flow channel. The outer sleeve includes an outer connection portion and a threaded portion with a sealing flange, while the inner sleeve includes an inner connection portion and a tapered portion. The tapered portion and the threaded portion are compatible with other attachments for supplying and recovering air through the air flow system. An air pump supply can connect to the threaded portion. In some embodiments, an O-ring can threadedly engage and seal the air pump supply to the outer sleeve. An air recovery unit can connect to the tapered portion of the inner sleeve. Air is delivered through the outer sleeve and collected through the inner sleeve.

Embodiments of the air flow system also include a proximal connector attached to the hose member closest to the treatment site of the inflammation. The proximal connector has an outer nozzle body with an outer nozzle body flow channel and an inner nozzle body with an inner nozzle body flow channel. Air is delivered through the outer nozzle body and collected through the inner nozzle body. In some versions, the flow path starts at the air pump supply, through the outer sleeve flow channel of the distal connector, through the exterior flow channel of the exterior flow tube, through the outer nozzle body flow channel of the proximal connector, to the treatment site, back to the inner nozzle body flow channel of the proximal connector, back through the interior flow channel of the interior flow tube, and returned to the air recovery unit. Temperature and speed along the flow path are controlled for effective therapeutic treatment at the treatment site.

Direction of the flow path is also affected by embodiments of the present invention. In particular, the proximal connector can include a dispersion head and nozzle head to change direction of flow for supplying and recovering. Controlling the flow path is further affected by the embodiments of the air flow system with a ring member and a stop member mounted around the proximal connector. In some versions, the ring member has a flanged rim concave toward the inner nozzle body. The flanged rim is cooperative with both the nozzle head and the dispersion head to further change the direction of supplied air. The direction changes can be randomized or preset, according to therapeutic recommendations for temperature and speed of air flow. A variety of settings can allow a prescribed range of temperatures and speeds to treat the inflammation for a therapy session.

Embodiments of the present invention include a system for air circulation therapy. The system for air circulation includes the air flow system in the context of therapeutic equipment for treating a patient. Air circulation or air circumvection therapy is heating and cooling of the therapy site or treatment site by air flow to reduce inflammation and joint stiffness. Embodiments of the system include a flow chamber having an interior volume and an opening. The proximal connector attaches to the opening for sealed engagement for supplying and recovering air through the flow chamber. A body attachment means is integral with the flow chamber for a body part to be inserted through the flow chamber. The system connects an air pump supply and an air recovery unit at the distal connector to complete the flow path of air. A temperature sensor and air flow sensor can be placed in proximity to the opening or treatment site, and a control means connected to the sensors adjusts the air pump supply and the air recovery unit according to data from the sensors. There may also be a filter for the recovered air to remove particulates, add scents, medications, analgesics, and other contaminants. Embodiments of the present invention include the method for treating inflammation at a treatment site. A body part with a treatment site is placed within the flow chamber. Once closed to the body part, the air pump supply initiates an air flow through the outer sleeve of the distal connector, through the exterior flow tube, through the outer nozzle body of the proximal connector, and to the treatment site in the flow chamber. Some air is returned from the flow chamber through the inner nozzle body of the proximal connector, through the interior flow tube, through the inner sleeve of the distal connector and back to an air recovery unit. The air treats the inflammation with heat or cold from the supplied air at the first temperature at a particular flow speed. Then, air is vented from the flow chamber at a second temperature to the air recovery unit. Sensors in the system can detect temperature and flow speed for adjustments, active control, or preset ranges of temperatures and speeds for a particular therapeutic treatment.

DETAILED DESCRIPTION OF THE INVENTION

Referring to FIGS. 1-9, embodiments of the air flow system 10 of the present invention supplies air and recovers air. The temperature of the air supplied and the air recovered are different. The air supplied can be supplied at a first temperature. The flow path traveled by the air supplied includes circulating around inflammation on a body part of a patient and returning to the air flow system. The air recovered is at a second temperature and is vented away from the inflammation.

Figure 1:
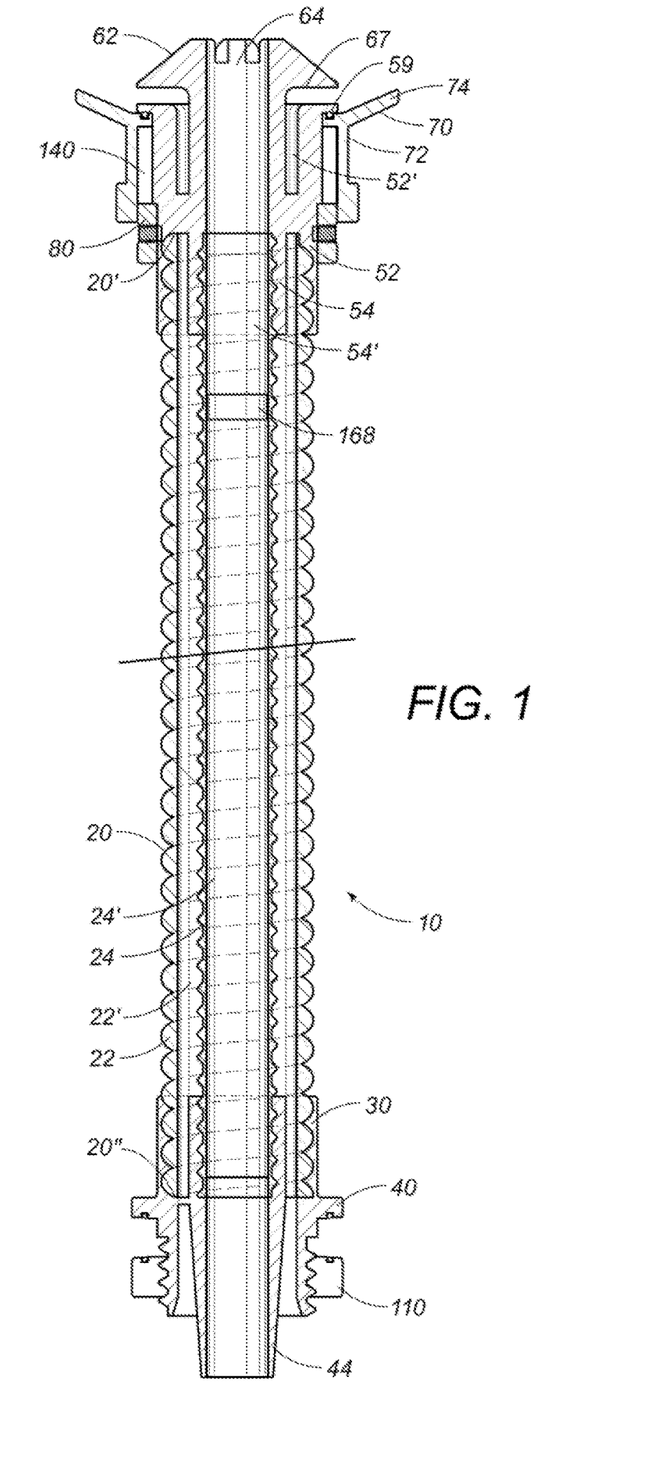
FIG. 1 is a sectional view of an embodiment of the air flow system, according to the invention.

Embodiments of the air flow system 10 include a hose member 20 having a proximal end 20' and a distal end 20" opposite the proximal end. The hose member can have an exterior flow tube 22 forming an exterior flow channel 22', and an interior flow tube 24 forming an inner flow channel 24'. FIG. 1 shows the hose member 20 as corrugated, although no particular surfacing is required by the present invention. The interior flow tube 24 can be concentrically aligned with the exterior flow tube 22 so that both tubes 22, 24 are on the same axis. FIG. 1 shows the interior flow tube 24 mounted within the exterior flow tube 22. The interior flow tube 24 and the exterior flow tube 22 may also be separate tubes. The interior flow channel 24' should be sealed with respect to the exterior flow channel 22' because the interior flow channel 24' recovers air, while the exterior flow channel 22' supplies or delivers air. The interior flow channel 24' may be within the exterior flow channel 22, but these flow channels 22', 24' are not in direct fluid communication within the hose member 20. The air supplied and the air recovered must be separate.

Figure 2:
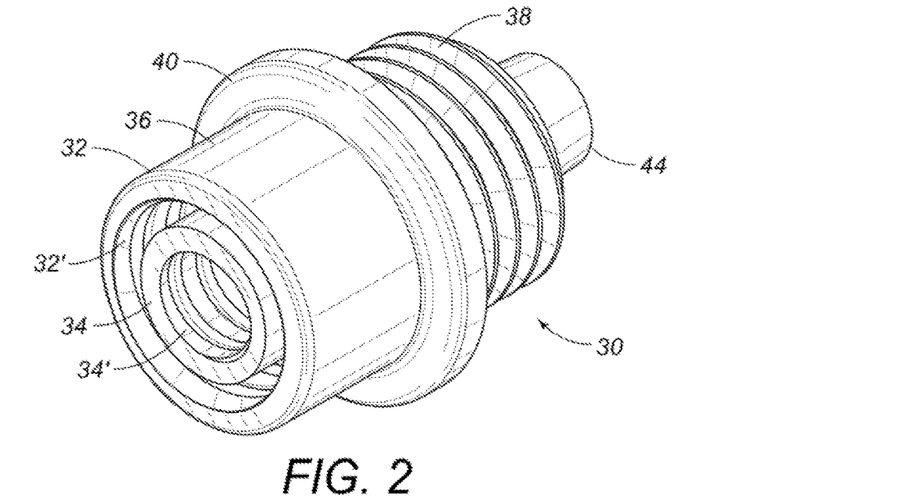
FIG. 2 is an upper perspective view of an embodiment of the distal connector of the air flow system of FIG. 1.
Figure 3:
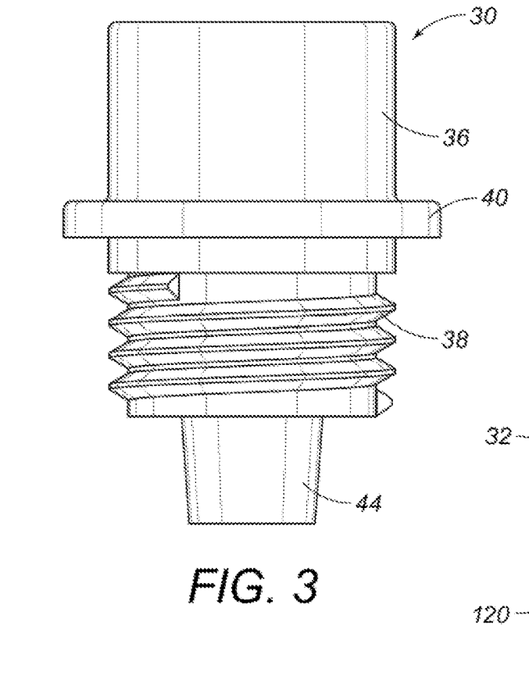
FIG. 3 is a side elevation view of the distal connector of FIG. 2.
Figure 4:
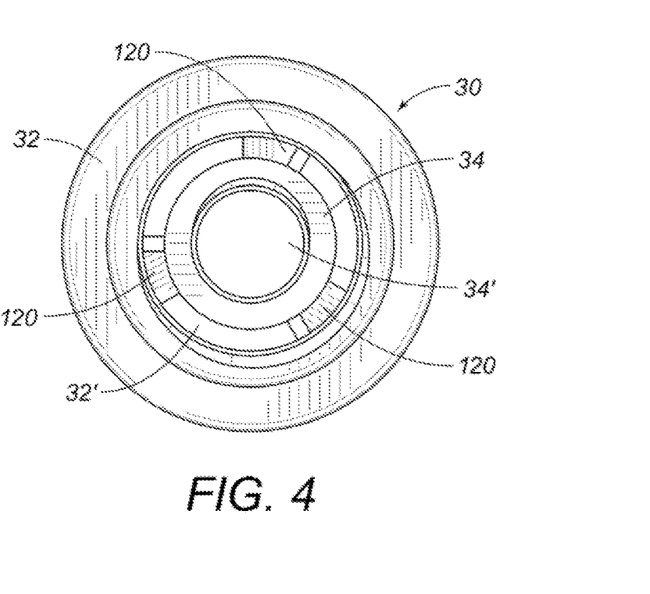
FIG. 4 is an end elevation view of the distal connector of FIG. 2.

FIGS. 1-4 shows embodiments of the distal connector 30 attached to the distal end 20" of the hose member 20. The distal connector 30 comprises an outer sleeve 32 having an outer sleeve flow channel 32', and an inner sleeve 34 having an inner sleeve flow channel 34'. The exterior flow channel 22' is in fluid connection with the outer sleeve flow channel 32', and the interior flow channel 24' is in fluid connection with the inner sleeve flow channel 34'. The outer sleeve 32 can have an outer connection portion 36 and a threaded portion 38 with a sealing flange 40. FIG. 1 shows how the outer connection portion 36 is friction fit or mechanically fit to the exterior flow tube 22. The threaded portion 38 is on the side opposite the hose member 20. The inner sleeve 34 can have an inner connection portion 42 and a tapered portion 44, and the inner connection portion 42 is friction fit to the interior flow tube 24, respectively. FIGS. 2 and 4 show the inner sleeve 34 concentrically aligned with and mounted within the outer sleeve 32.

FIG. 2 shows the inner connection portion 42 and the outer connection portion 36 flush to the end of the distal connector 30. The hose member 20 can insert into the distal connector 30 evenly. FIGS. 3 and 4 show the other side of the distal connector with the tapered portion 44 protruding through the threaded portion 38. The tapered portion 44 and the threaded portion 38 with flange 40 are compatible with other attachments for supplying and recovering air through the air flow system 10. For example, an air pump supply means 100 of FIG. 12 can be removeably connected to the threaded portion 38 and in fluid connection with the outer sleeve flow channel 32'. Consequently, an O-ring 110 in FIGS. 1 and 9 can threadedly engage on the threaded portion 38, sealing the air pump supply means 100 to the outer sleeve 32. For the inner sleeve 34, an air recovery unit means 130 of FIG. 12 can be removeably connected to the tapered portion 44 and in fluid connection with the inner sleeve flow channel 34'. Air is delivered through the outer sleeve 32 and collected through the inner sleeve 34, corresponding to the exterior flow tube 22 and the interior flow tube 24. Like the flow channels 22', 24', the inner sleeve flow channel 34' may be within the outer sleeve flow channel 32', but these flow channels 32', 34' are not in direct fluid communication within the distal connector 30.

FIG. 4 shows another embodiment with a plurality of baffles 120 between an interior surface of the outer sleeve 32 and an exterior surface of the inner sleeve 34. Each baffle 120 can be curved so as to direct air to the proximal end 20' of the hose member 20 from the distal connector 30. A curve or twist to increase air speed or obstructing shapes to slow air speed are each possible. Baffles 120 are within the outer sleeve flow channel 32' and can support the alignment of the inner sleeve 34 and interior flow tube 24 relative to the outer sleeve 32 and the exterior flow tube 22.

Figure 5:
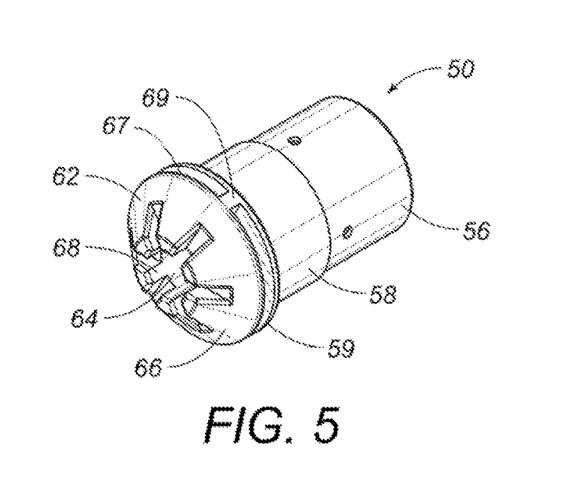
FIG. 5 is an upper perspective of an embodiment of the proximal connector of the air flow system of FIG. 1.
Figure 6:
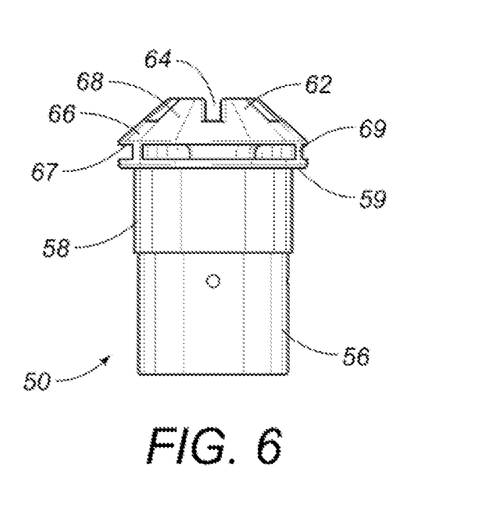
FIG. 6 is a side elevation view of the proximal connector of FIG. 5.

FIGS. 1, 5 and 6 show embodiments of a proximal connector 50 of the air flow system 10. The proximal connector 50 attaches to the proximal end 20' of the hose member 20. The proximal end 20' is closest to the treatment site of the inflammation. The proximal connector 50 is typically closer to the body part of the patient. FIG. 1 shows the proximal connector 50 comprising an outer nozzle body 52 having an outer nozzle body flow channel 52' and an inner nozzle body 54 having an inner nozzle body flow channel 54'. There are two flow channels again. Similarly, air is delivered through the outer nozzle body 52 and collected through the inner nozzle body 54, corresponding to the exterior flow tube 22/outer sleeve 32 and the interior flow tube 24/inner sleeve 34. Like the flow channels 22', 24', 32', 34', the inner nozzle body flow channel 54' may be within the outer nozzle body flow channel 32', but these flow channels 52', 54' are separate. These flow channels 52', 54' are not in direct fluid communication in the proximal connector 50, but there can be fluid communication via the treatment site. The flow path starts at the air pump supply means 100, through the outer sleeve flow channel 32' of the distal connector 30, through the exterior flow channel 22' of the exterior flow tube 22, through the outer nozzle body flow channel 52' of the proximal connector 50, to the treatment site, back to the inner nozzle body flow channel 54' of the proximal connector 50, back through the interior flow channel 24' of the interior flow tube 24, and returned to the air recovery unit means 130. The temperature and speed along the flow path are controlled for effective therapeutic treatment at the treatment site.

FIGS. 5-6 show the outer nozzle body 52 being comprised of an outer attachment portion 56 and a dispersion head 58. The exterior flow tube 22 is friction fit to the outer attachment portion 56 in FIG. 1 with the exterior flow channel 22' being in fluid connection with the outer nozzle body flow channel 52'. FIG. 1 also shows the inner nozzle body 54 being comprised of an inner attachment portion 60 and a nozzle head 62. The interior flow tube 24 is friction fit to the inner attachment portion 60 with the interior flow channel 24' being in fluid connection with the inner nozzle body flow channel 54'. FIGS. 1, 5 and 6 show the nozzle head 62 with an aperture 64 in fluid connection with the inner nozzle body flow channel 54'.

Embodiments of the nozzle head 2 includes a generally frustoconical cap 66 with a toothed aperture 68, as in FIGS. 5-6. The drag and air speed of the toothed aperture 68 can be adjusted by changing the aperture 64 or by changing air speed or both, depending upon the treatment recommendation or range of speeds needs at particular temperatures. FIG. 1 shows an embodiment compatible with the dispersion head 58 being comprised of a flange 59 perpendicular to the outer nozzle body 52. The nozzle head 62 and the dispersion head 58 cooperatively direct the outer nozzle body flow channel 52' perpendicular to the inner nozzle body flow channel 54'. The misdirection is important to avoid turbulence and directly recovering the air supplied. The air from the dispersion head 58 must reach the treatment site before being vented back to the aperture 64. FIGS. 1, 5 and 6 further show a back side 67 of the cap 66 being aligned with the flange 59 of the dispersion head 58 to maintain this flow path perpendicular to the flow channels 54', 34' and 24' for recovering air. A plurality of spacers 69 can also be seen in FIGS. 5-6 between the flange 59 of the dispersion head 58 and the back side 67 of the cap 66. The spacers 69 can be distributed around a circumference of the inner nozzle body 54.

Figure 7:
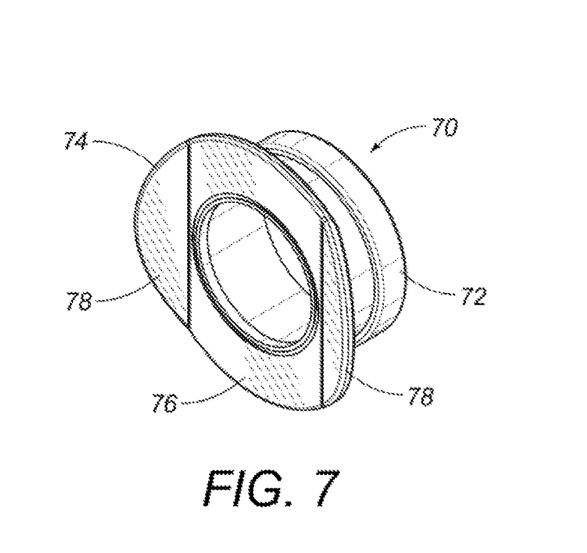
FIG. 7 is an upper perspective view of an embodiment of the ring member of the air flow system of FIG. 1.
Figure 8:
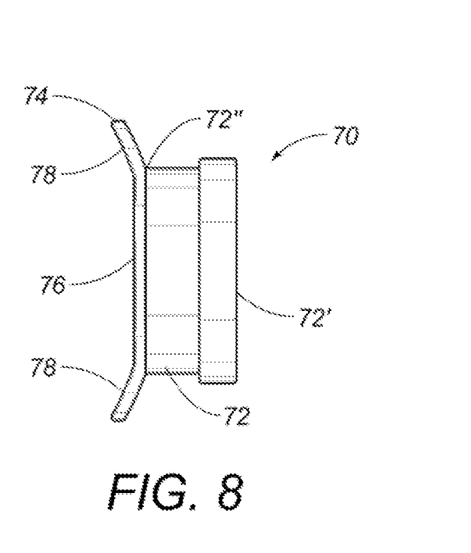
FIG. 8 is a side elevation view of the ring member of FIG. 5.
Figure 9:
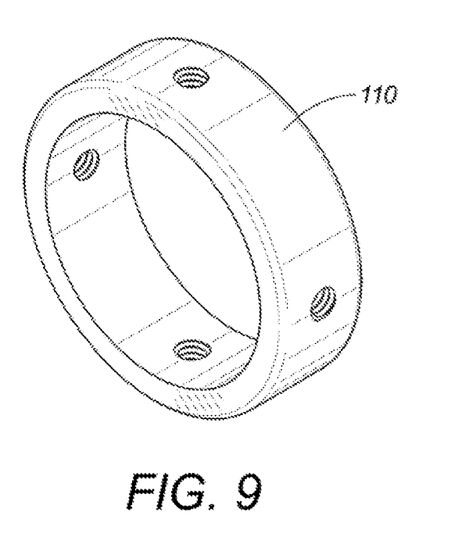
FIG. 9 is an upper perspective view of an embodiment of an O-ring for attachment to the threaded portion of the distal connector.

Controlling the flow path is further affected by the embodiments of the air flow system 10 with a ring member 70 mounted around the proximal connector 50. Other prior art only increases or decrease speed or temperature, without additional structures to interact with the effectiveness and efficiencies of these dimensions. The present invention delivers more than hot air to the treatment site by controlling flow path and hot air at different speeds. The ring member 70 is shown in FIGS. 1, 7 and 8 as a ring body 72 being engaged around the proximal connector 50. The ring body 72 has a first end 72' and a second end 72", and there is a flanged rim 74 on the first end 72'.

Embodiments of the ring member 70 show the flanged rim 74 as concave toward the aperture 64 of the inner nozzle body 54. One version has the flanged rim 74 comprised of a planar section 76 and two curved sections 78 on both sides of the planar section 76. The flanged rim 74 is adjacent the dispersion head 58 in FIG. 1. The flange 59 and the flanged rim 74 can direct the air from the outer nozzle body channel 52'. The flanged rim 74 is cooperative with the nozzle head 62 and the dispersion head 58 to change the outer nozzle body flow channel 52' from perpendicular to the other flow channels 54', 34', and 24' for recovering air. The ring member 70 can be rotatable for randomizing the spray of air from the dispersion head 58. The randomization prevents air flow from releasing directly from the dispersion head 58 to return to the aperture 64. The speed and direction can rotate at different rates sufficient to deliver the air of a particular speed and temperature to the treatment site.

Figure 10:
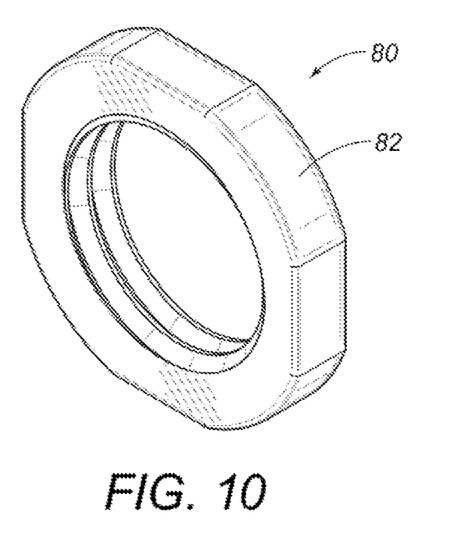
FIG. 10 is an upper perspective view of an embodiment of a stop member for setting the ring member relative to the proximal connector.

FIGS. 1 and 10 also show a stop member 80 mounted around the proximal connector 50. The stop member 80 can be comprised of a cylindrical body 82 being engaged around the proximal connector 50 and abutted against the second end 72" of the ring member 70 so as to set a position of the ring member 70 relative to inner nozzle body 54, in particular, the cap 66 of the inner nozzle body 54. The stop member 80 is also cooperative with the ring member 70 to change the flow path from the dispersion head 58 to the treatment site and eventually back to the aperture 64 for recovery. FIG. 1 shows one embodiment with a spring means 140 housed within the ring member 70. The spring means 140 can be a compression spring, tension spring or other known elastic element engaging the stop member 80 and the ring member 70 so as to exert pressure against the dispersion head 58 by the flanged rim 74. Faster air may push the flanged rim 74 further away from the dispersion head 58, changing the deviation from perpendicular of the flange 59. Slower air may not resist the spring means 80 as much, for yet another different flow path to the treatment site. A variety of settings can allow a prescribed range of temperatures and speeds to treat the inflammation for a therapy session.

Figure 11:
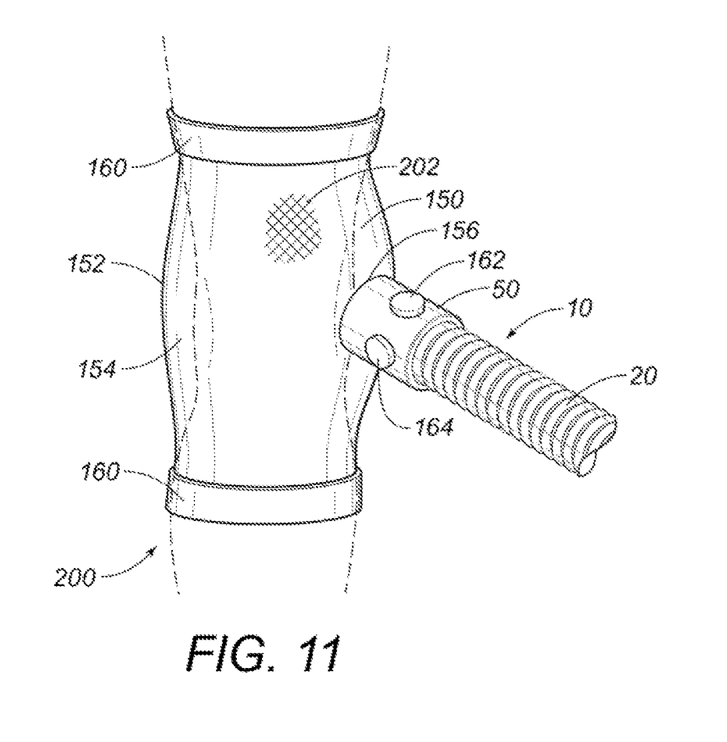
FIG. 11 is a perspective view of the system for circulation therapy, show a patient's limb in a flow chamber or cuff.
Figure 12:
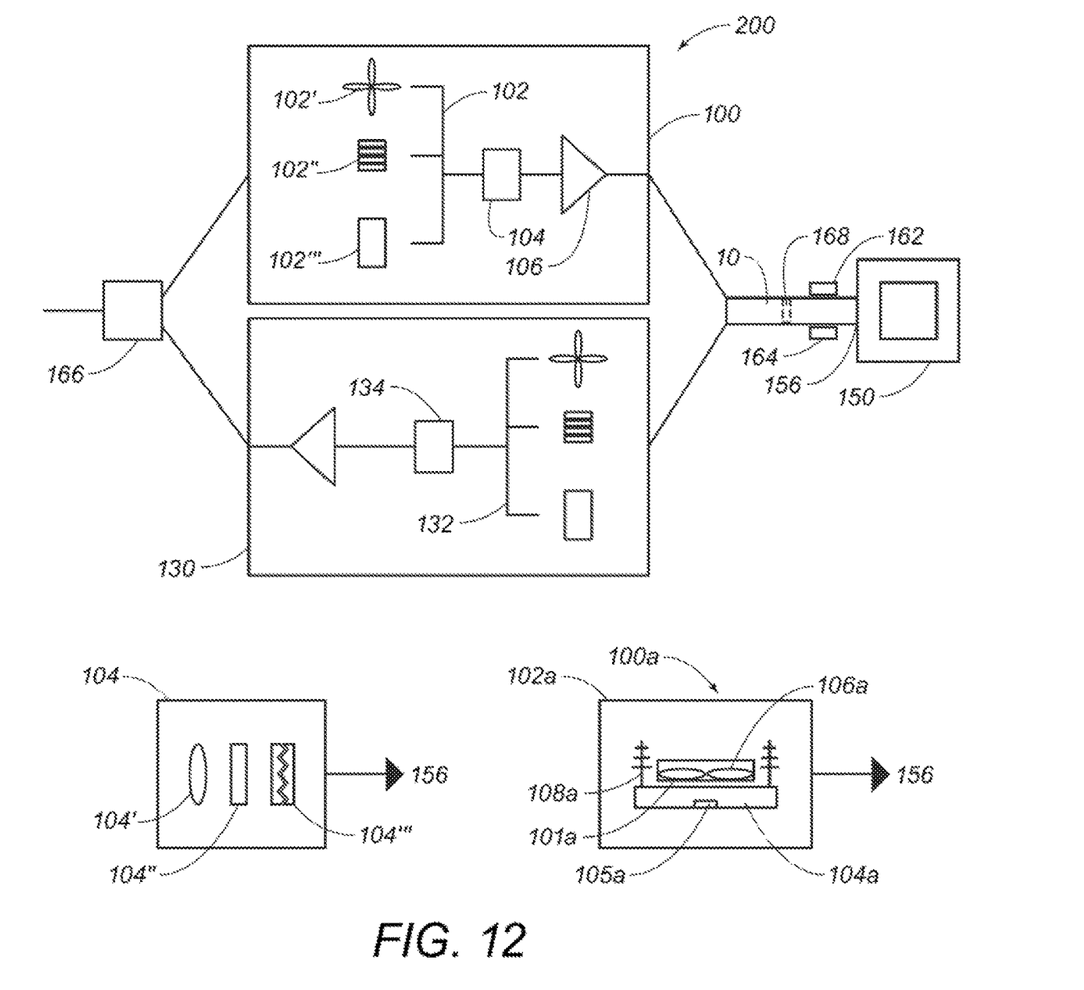
FIG. 12 is a schematic view of the system for circulation therapy, show adjustments of air speed and air temperature, according to treatment recommendations.

The present invention also includes the system 200 for air circulation therapy. The system 200 for air circulation therapy includes the air flow system 10 in the context of therapeutic equipment for treating a patient. Air circulation or air circumvection therapy is heating and cooling of the therapy site or treatment site 202 by air flow to reduce inflammation and joint stiffness. Other uses of a temperature regulated environment are also possible. The temperature controlled therapy of the prior art, such as ice packs and heating pads, require surface contact with the injured tissue. Treatment of open wounds or injuries within a joint was not possible or ineffective. Other air flow therapies relied on compression from air pressure to treat inflammation or only use air temperature for treatment. In the present invention, moving air with convection effects more efficiently treat the injury. The temperature controlled moving air of different speeds of the present invention penetrates heating or cooling into injured tissue deeper than surface treatments. The system 200 delivers heated or cooled air at various speeds to address inflammation or other health conditions. FIGS. 11-12 show the system 200 for air circulation therapy being comprised of the air flow system 10.

There is also a flow chamber 150 being comprised of a surface wall 152 defining an interior volume 154, and an opening 156. The flow chamber 150 has an expanded configuration and a collapsed configuration, depending upon the amount of air supplied by the air flow system 10. The expanded configuration is an inflated setting with the surface wall 152 not in contact with the body part or therapy site. The flow chamber 150 also has a collapsed configuration with less air flow through the interior volume 154 than the expanded configuration. The deflated setting with the collapsed configuration has less air flow or no air flow so that the flow chamber 150 can be removed from the body part. There may be contact against the body part by the surface wall 152 in the collapsed configuration.

FIG. 11 shows the proximal connector 50 removably attached to the opening 156 for sealed engagement between the exterior flow tube 22 and the flow chamber 150 and fluid connection between the flow chamber 50 and the exterior flow tube channel 22' and the interior flow tube channel 24' of the hose member 20.

The body attachment means 160 is also shown in FIG. 11 as being made integral with the flow chamber 150 for a body part to be inserted through the flow chamber 150. FIG. 11 shows a body part as a knee with the treatment site 202 on a knee joint. The moving air at a certain temperature is supplied to the treatment site 202 by the hose member 20 through the proximal connector 50. The body attachment means 160 can initially sets the interior volume 154 of the flow chamber 150 by closing top and bottom ends of the flow chamber 150 to the body part. By setting the interior volume 154, the expanded configuration and the collapsed configuration are also set. FIG. 11 shows the body attachment means 160 as an elastic band. Other known body attachment means 160 include a strap with a hook and loop fastener, a drawstring, snap fit connectors, friction fit bands, and adhesives. The body attachment means 160 must form a generally tight seal against the body part so that the flow path of the air from the air flow system reaches the treatment site 202. Too much leaking at the body attachment means 160 may reduce effectiveness, but there is no requirement for an air tight seal, and the body attachment means 160 does not maintain any particular pressure in the interior volume. The pressure may even change as the range of temperatures and speeds are experienced by the patient during treatment.

The system 200 further comprises an air pump supply means 100 being removeably connected to the threaded portion 38 and being in fluid connection with the outer nozzle body flow channel 52'; and an air recovery unit means 130 being removeably connected to the tapered portion 44 and being in fluid connection with the inner sleeve flow channel 34'.

In some embodiments, the air pump supply means 100 can be the air recovery unit means 130, depending upon the thermodynamics of the air flow speed and air temperature to be delivered to the treatment site 202. Generally, the air pump supply means 100 is comprised of a fan means 102 and a temperature regulation means 104, as in FIG. 12. The fan means 102 of the air pump supply means 100 can include a pump 102''', a fan 102', blower 102" or other device. There can also be an accelerator 106 for additionally regulating the speed of air. The temperature regulation means 104 can include a heat exchanger 104''', radiator 104", a compressor 104' or other device. Any known heat exchanger 104''' can be used, such as one with the air passing over a coiled tube of a set temperature. Thus, the air pump supply means 100 generates air flow of a certain temperature with the temperature regulation means 104. Heated air and cooled air can be generated at a particular speed. Similarly, the air recovery unit means 130 can be comprised of a respective fan means 132 and a respective temperature regulation means 134. The respective fan means 132 may also be a pump, fan, blower or other device, and the respective temperature regulation means 134 may also be a heater, heat exchanger, compressor, or other device. The air recovery unit means 130 receives the vented exhaust from the treatment site 202, so that air may be hotter or cooler than the air delivered by the air pump supply means 100.

An alternative embodiment of the air pump supply means 100*a* is shown in FIG. 12. The air pump supply means 100*a* is comprised of a thermoelectric coupler 102*a*, a base plate 104*a*, impeller 106*a*, and stationary fins 108*a*. The coupler 102*a* can be heat sink for a circuit or other electronic heating or cooling element 105*a*. The thermoelectric coupler 102*a* transfers heat to the base plate 104*a*. In other embodiments, the thermoelectric coupler 102*a* transfers heat from the base plate 104*a* for cooling. The base plate 104*a* and the impeller 106*a* are separated by an air gap 101*a* for heat transfer across the air gap 101*a*. Air can enter an intake through rotation of the impeller 106*a*. The air can be atmospheric air for open loop configuration or from the inner sleeve flow channel 34' of the distal connector 30 for closed loop configuration. Then, the air flows to the air gap 101*a* between the impeller 106*a* and the base plate 104*a*. The heat transfer can be heating or cooling with the base plate 104*a* dissipating heat or gathering heat from the air in the air gap. The heated or cooled air flows from the air gap 101*a* to the stationary fins 108*a*. In some embodiments, air passes through the stationary fins 108*a* to the outer sleeve flow channel 32' of the distal connector 30. The heated air or the cooled air in the air gap 101*a* can be directed to the treatment site 202 through the system 200. The impeller 106*a* flows air from the atmosphere and from the air gap 101*a* through the stationary fins 108*a*. The combined source of air is more efficient because the heated air from the air gap 101*a* is already hotter than the atmospheric air for heating. The cooled air from the air gap 101*a* is already cooler than the atmospheric air for cooling through the stationary fins 108*a*. The stationary fins 108*a* are no longer the sole source of heat transfer for the atmospheric air pulled in by the impeller 106*a*. The fully heated air or cooled air from the atmosphere and the air gap passes through the stationary fins. The air gap heating and dissipation for temperature regulation is another possible temperature regulation means 104. Instead of being a heat sink for wasted heat, the present invention incorporates thermoelectric heat for more efficient heating and cooling temperature regulation by air movement.

FIG. 12 suggests embodiments include open loop and closed loop configurations. An embodiment of a closed loop configuration includes the air pump supply means 100 being the air recovery unit means 130 at the same time, with the controlled air blown from one end (outer sleeve flow channel 32') and the vented exhaust air recycled from the other end (inner nozzle body flow channel 54'). The thermodynamics of such an embodiment are a major consideration in the energy exchange and loss. Even if a closed loop, the system 200 is not a closed system. Energy added and loss would need to be addressed. FIG. 12 shows an embodiment with an open loop configuration with the air pump supply means 100 and the air recovery unit means 130 separate, but a closed loop configuration remains possible with the various baffles, springs, and obstacles for flow speed.

FIGS. 11-12 also show the system 200 having a temperature sensor 162 and air flow sensor 164 positioned in fluid connection with the flow chamber 150. These sensors 162, 164 can be in proximity to the opening 156 or treatment site 202. FIG. 12 includes a control means 166 connected to the air pump supply means 100, the air recovery unit means 130, the temperature sensor 162 and the air flow sensor 164 to collect feedback data from the sensors 162, 164. The control means 166 adjusts the air pump supply means 100 and the air recovery unit means 130 according to the collected data. The system 200 is more efficient, and not as much heat may be needed for a desired temperature regulation. Still another embodiment includes a filter 168 in fluid connection with the air through the inner nozzle body flow channel 54'. Air entering the hose member 22 may need to be filtered to remove particulates, add scents, medications, analgesics, and other contaminants. A filter 168 can be placed between the nozzle head 62 of the proximal connector and the inner sleeve 34 of the distal connector 30.

Embodiments of the present invention include the method for treating inflammation at a treatment site 202. The air flow system 10 is assembled, and the proximal connector 50 is attached to a flow chamber 150 so that the exterior flow tube channel 22' and the interior flow tube channel 24' are in fluid connection with the interior volume 154. A body part with the treatment site 202 is inserted within the flow chamber 150, and then, the flow chamber is closed or sealed to the body part with the treatment site within the interior volume 154. An air pump supply means 100 is connected to the threaded portion 38 for fluid connection with the outer sleeve flow channel 32', and an air recovery unit means 130 is connected to the tapered portion 44 for fluid connection with the inner sleeve flow channel 34'. Air flows from the air pump supply means 100 to the flow chamber 150 at a first temperature through the exterior flow tube 22 so as to fill the flow chamber 150. The air treats the inflammation with heat or cold at a particular flow speed. Then, air is vented from the flow chamber at a second temperature through the interior flow tube 24 to the air recovery unit means 130. When a temperature sensor 162 and an air flow sensor 164 are mounted in fluid connection with the flow chamber 150, the collected feedback data from the temperature sensor and the air flow sensor confirm the first temperature and the second temperature and other parameters. The air pump supply means and the air recovery unit means can be adjusted according to the feedback data by a control means connected to the air pump supply means, the air recovery unit means, the temperature sensor and the air flow sensor. Besides temperature, flow rate of the air pump supply means and air recovery unit means may also be used to make adjustments to the air pump supply means and air recovery unit means.

The present invention provides a system and method for a flow chamber with air flow of a particular temperature and speed. Treatment of inflammation and therapeutic uses for joints are examples of practical uses of the system, but other applications are possible. Air circulation or air circumvection of the system uses heating and cooling from moving air to reduce inflammation at the therapy or treatment site. Movement of air, not just temperature and pressure of air, can be used in other fields. Air convection with controlled temperature and speed of air flow along the flow path of the present invention provides moving heated or cooled air to a therapy site on the body part. The temperature controlled therapy is based on moving air, not just heated air. The convection currents more thoroughly and deeply penetrate into injured tissue without the risk of cold burns and other surface contact risks to the body part. The system provides controlled air flow and temperature control for treating inflammation.

Embodiments of the present invention supply air at a first temperature and first speed and recover air at a second temperature and a second speed from a flow chamber. The inflammation or other treatment site in the flow chamber receives the heat or cold and air movement for treatment. With the flow chamber closed, some of the air can be recovered or at least recycled back into the system. The flow path of air in the system includes air supplied to the flow chamber and air recovered from the flow chamber. Before the recovery, the treatment site, such as inflammation, on a patient's body is exposed to air flow at a regulated temperature, speed, and direction. The air flow speed and air temperature together can be changed together or separate for desired therapeutic effects.

The foregoing disclosure and description of the invention is illustrative and explanatory thereof. Various changes in the details of the illustrated structures, construction and method can be made without departing from the true spirit of the invention.

I claim:

1. An air flow system, comprising:
   hose member having a proximal end and a distal end opposite said proximal end, said hose member being comprised of an exterior flow tube forming an exterior flow channel, and an interior flow tube forming an inner flow channel, said interior flow tube being concentrically aligned with and mounted within said exterior flow tube, said inner flow channel being sealed with respect to said exterior flow channel;
   a distal connector attached to said distal end of said hose member, wherein said distal connector comprises an outer sleeve having an outer sleeve flow channel, and an inner sleeve having an inner sleeve flow channel,
   wherein said outer sleeve is comprised of: an outer connection portion and a threaded portion with a sealing flange, said outer connection portion being friction fit to said exterior flow tube, said exterior flow channel being in fluid connection with said outer sleeve flow channel, and
   wherein said inner sleeve is comprised of: an inner connection portion and a tapered portion, said inner connection portion being friction fit to said interior flow tube, said interior flow channel being in fluid connection with said inner sleeve flow channel, said inner sleeve being concentrically aligned with and mounted within said outer sleeve; and
   a proximal connector attached to said proximal end of said hose member, wherein said proximal connector comprises: an outer nozzle body having an outer nozzle body flow channel; and an inner nozzle body having an inner nozzle body flow channel,
   wherein said outer nozzle body is comprised of an outer attachment portion and a dispersion head, said exterior flow tube being friction fit to said outer attachment portion, said exterior flow channel being in fluid connection with said outer nozzle body flow channel,
   wherein said inner nozzle body is comprised of an inner attachment portion and a nozzle head, said interior flow tube being friction fit to said inner attachment portion, said interior flow channel being in fluid connection with said inner nozzle body flow channel,
   wherein said nozzle head has an aperture in fluid connection with said inner nozzle body flow channel,
   a ring member mounted around said proximal connector, said ring member being comprised of a ring body being engaged around said proximal connector and having a first end and a second end, and a flanged rim on said first end,
   wherein said flanged rim is concave toward said aperture of said inner nozzle body; and a stop member mounted around said proximal connector, said stop member being comprised of a cylindrical body being engaged around said proximal connector and abutted against said second end of said ring member so as to set a position of said ring member relative to the cap of said inner nozzle body.

2. The air flow system, according to claim 1, wherein said inner connection portion aligns with said outer connection portion, said tapered portion protruding through said threaded portion, said interior flow channel and said interior flow tube being within said exterior flow channel.

3. The air flow system, according to claim 1, further comprising: an air pump supply means being removeably connected to said threaded portion and being in fluid connection with said outer sleeve flow channel.

4. The air flow system, according to claim 1, further comprising: an O-ring threadedly engaged on said threaded portion, said O-ring sealing said air pump supply means to said outer sleeve.

5. The air flow system, according to claim 1, further comprising: a plurality of baffles between an interior surface of said outer sleeve and an exterior surface of said inner sleeve.

6. The air flow system, according to claim 5, where each baffle has a curved shape so as to direct flow to said proximal end of said hose member.

7. The air flow system, according to claim 1, further comprising: an air recovery unit means being removeably connected to said tapered portion and being in fluid connection with said inner sleeve flow channel.

8. The air flow system, according to claim 1, wherein said nozzle head is comprised of a generally frustoconical cap with a toothed aperture, and wherein said dispersion head is comprised of a flange perpendicular to said outer nozzle body.

9. The air flow system, according to claim 8, wherein a back side of the cap of said nozzle head is aligned with said flange.

10. The air flow system, according to claim 9, further comprising a plurality of spacers between said flange and said back side of the cap.

11. The air flow system, according to claim 1, wherein said nozzle head and said dispersion head cooperatively direct said outer nozzle body flow channel perpendicular to said inner nozzle body flow channel.

12. The air flow system, according to claim 1, wherein said flanged rim is comprised of a planar section and two curved sections on both sides of said planar section.

13. The air flow system, according to claim 12, wherein said flanged rim is cooperative with said nozzle head and said dispersion head to change said outer nozzle body flow channel from perpendicular.

14. The air flow system, according to claim 1, further comprising: a spring means housed within said ring member, said spring means engaging said stop member and said ring member so as to exert pressure against said dispersion head by said flanged rim.

15. A method for treating inflammation at a treatment site, said method comprising the steps of:
assembling the air flow system, according to claim 1;
attaching said proximal connector to a flow chamber being comprised of a surface wall defining an interior volume, and an opening, said flow chamber having an expanded configuration and a collapsed configuration, said flow chamber being in fluid connection between said exterior flow tube channel and said interior flow tube channel,
wherein said proximal connector is removably attached to said opening for sealed engagement between said exterior flow tube and said flow chamber and fluid connection between said exterior flow tube and said flow chamber and between said interior flow tube and said flow chamber,
inserting a body part with the treatment site within said flow chamber;
sealing said flow chamber to the body part with the treatment site within said interior volume;
connecting an air pump supply means to said threaded portion and being in fluid connection with said outer sleeve flow channel;
connecting an air recovery unit means to said tapered portion and being in fluid connection with said inner sleeve flow channel;
flowing air from said air pump supply means to said flow chamber at a first temperature through said exterior flow tube so as to fill said flow chamber; and
venting air from said flow chamber at a second temperature through said interior flow tube to said air recovery unit means.

16. The method for treating inflammation at a treatment site, according to claim 15, further comprising the steps of:
mounting a temperature sensor and an air flow sensor in fluid connection with said flow chamber;
collecting feedback data from said temperature sensor and said air flow sensor so as to confirm said first temperature and said second temperature; and
adjusting said air pump supply means and said air recovery unit means according to said feedback data.

17. A system for air circulation therapy, comprising:
hose member having a proximal end and a distal end opposite said proximal end, said hose member being comprised of an exterior flow tube forming an exterior flow channel, and an interior flow tube forming an inner flow channel, said interior flow tube being concentrically aligned with and mounted within said exterior flow tube, said inner flow channel being sealed with respect to said exterior flow channel;
a distal connector attached to said distal end of said hose member, wherein said distal connector comprises an outer sleeve having an outer sleeve flow channel, and an inner sleeve having an inner sleeve flow channel,
wherein said outer sleeve is comprised of: an outer connection portion and a threaded portion with a sealing flange, said outer connection portion being friction fit to said exterior flow tube, said exterior flow channel being in fluid connection with said outer sleeve flow channel, and
wherein said inner sleeve is comprised of: an inner connection portion and a tapered portion, said inner connection portion being friction fit to said interior flow tube, said interior flow channel being in fluid connection with said inner sleeve flow channel, said interior flow channel being concentrically aligned with and mounted within said outer sleeve;
a proximal connector attached to said proximal end of said hose member, wherein said proximal connector comprises: an outer nozzle body having an outer nozzle body flow channel; and an inner nozzle body having an inner nozzle body flow channel,
wherein said outer nozzle body is comprised of an outer attachment portion and a dispersion head, said exterior flow tube being friction fit to said outer attachment portion, said exterior flow channel being in fluid connection with said outer nozzle body flow channel, wherein said inner nozzle body is comprised of an inner attachment portion and a nozzle head, said interior flow tube being friction fit to said inner attachment portion, said interior flow channel being in fluid connection with said inner nozzle body flow channel, wherein said nozzle head has an aperture in fluid connection with said inner nozzle body flow channel;

a ring member mounted around said proximal connector, said ring member being comprised of a ring body being engaged around said proximal connector and having a first end and a second end, and a flanged rim on said first end, wherein said flanged rim is concave toward said aperture of said inner nozzle body;

a stop member mounted around said proximal connector, said stop member being comprised of a cylindrical body being engaged around said proximal connector and abutted against said second end of said ring member so as to set a position of said ring member relative to said inner nozzle body;

a flow chamber being comprised of a surface wall defining an interior volume, and an opening, said flow chamber having an expanded configuration and a collapsed configuration, said flow chamber being in fluid connection between said exterior flow tube channel and said interior flow tube channel, wherein said proximal connector is removably attached to said opening for sealed engagement between said exterior flow tube and said flow chamber and fluid connection between said exterior flow tube and said flow chamber and between said interior flow tube and said flow chamber;

a body attachment means made integral with said flow chamber;

an air pump supply means being removeably connected to said threaded portion and being in fluid connection with said outer sleeve flow channel;

an air recovery unit means being removeably connected to said tapered portion and being in fluid connection with said inner sleeve flow channel;

a temperature sensor positioned in fluid connection with said flow chamber;

an air flow sensor positioned in fluid connection with said flow chamber; and a control means connected to said air pump supply means, said air recovery unit means, said temperature sensor and said air flow sensor.

18. The system for air circulation therapy, according to claim 17, wherein said air pump supply means is comprised of a fan means and a temperature regulation means, and wherein said air recovery unit means is comprised of another fan means and another temperature regulation means.

19. The system for air circulation therapy, according to claim 17, wherein said air pump supply means is comprised of a thermoelectric coupler, a base plate, impeller, and stationary fins, wherein said thermoelectric coupler is configured to transfers heat to said base plate, wherein said base plate and the impeller are separated by an air gap, wherein the base plate is configured to transfer heat to air located in the air gap to generate heated air, wherein said impeller is configured to propel air from the atmosphere and from said air gap through said stationary fins, and into said outer sleeve flow channel.

20. The system for air circulation therapy, according to claim 17, further comprising: a filter between said nozzle head of said inner nozzle body and said distal connector.

* * * * *